United States Patent
Wu et al.

(10) Patent No.: US 11,292,841 B2
(45) Date of Patent: Apr. 5, 2022

(54) ANTI-PD-1 NANO-ANTIBODY AND APPLICATION THEREOF

(71) Applicant: ZHEJIANG TERUISI PHARMACEUTICAL INC., Zhejiang (CN)

(72) Inventors: Youling Wu, Zhejiang (CN); Yujie Zhang, Zhejiang (CN); Xiaolin Chen, Zhejiang (CN); Binbin Shen, Zhejiang (CN); Xiaoning Shen, Zhejiang (CN)

(73) Assignee: ZHEJIANG TERUISI PHARMACEUTICAL INC., Zhejiang (CN)

( * ) Notice: Subject to any disclaimer, the term of this patent is extended or adjusted under 35 U.S.C. 154(b) by 526 days.

(21) Appl. No.: 16/333,408

(22) PCT Filed: Sep. 11, 2017

(86) PCT No.: PCT/CN2017/101274
§ 371 (c)(1),
(2) Date: Jul. 8, 2019

(87) PCT Pub. No.: WO2018/050039
PCT Pub. Date: Mar. 22, 2018

(65) Prior Publication Data
US 2019/0322747 A1    Oct. 24, 2019

(30) Foreign Application Priority Data

Sep. 14, 2016 (CN) .......................... 201610827021.X

(51) Int. Cl.
*C07K 16/28* (2006.01)
*A61K 39/395* (2006.01)
*A61P 35/00* (2006.01)

(52) U.S. Cl.
CPC ...... *C07K 16/2818* (2013.01); *C07K 16/2827* (2013.01); *C07K 2317/14* (2013.01); *C07K 2317/24* (2013.01); *C07K 2317/565* (2013.01); *C07K 2317/567* (2013.01); *C07K 2317/569* (2013.01); *C07K 2317/76* (2013.01)

(58) Field of Classification Search
None
See application file for complete search history.

(56) References Cited

FOREIGN PATENT DOCUMENTS

| CN | 101312988 A | 11/2008 | |
|---|---|---|---|
| CN | 101410412 A | 4/2009 | |
| CN | 103242448 A | 8/2013 | |
| CN | 105339389 A | 2/2016 | |
| CN | 105683217 A | 6/2016 | |
| CN | 110835375 * | 2/2020 | ......... C07K 16/2818 |
| EP | 2899208 A1 | 7/2015 | |
| WO | 2004041867 A2 | 5/2004 | |
| WO | 2009121948 A2 | 10/2009 | |

* cited by examiner

*Primary Examiner* — Ilia I Ouspenski
(74) *Attorney, Agent, or Firm* — Novick, Kim & Lee, PLLC; Zhi Yang Xue; Bin Lu

(57) ABSTRACT

An anti-PD-1 nano-antibody capable of blocking a binding interaction between PD-1 and a ligand thereof, PD-L1. Disclosed are the nano-antibody, a nucleotide sequence encoding the nano-antibody, a corresponding expression vector, a host cell expressing the nano-antibody, and a method of producing the nano-antibody. Also disclosed is a humanized PD-1 nano-antibody sequence. The humanized nano-antibody can block the binding interaction between PD-1 and the ligand thereof, PD-L1 while still retaining a high affinity.

11 Claims, 6 Drawing Sheets

Specification includes a Sequence Listing.

SEQUENCE LISTING

<160> NUMBER OF SEQ ID NOS: 15

<210> SEQ ID NO 1
<211> LENGTH: 25
<212> TYPE: PRT
<213> ORGANISM: Camelus Linnaeus

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Val Ala Ser
            20                  25

<210> SEQ ID NO 2
<211> LENGTH: 15
<212> TYPE: PRT
<213> ORGANISM: Camelus Linnaeus

<400> SEQUENCE: 2

Trp Phe Arg Gln Val Pro Asp Lys Glu Arg Glu Gly Val Ala Ala
1               5                   10                  15

<210> SEQ ID NO 3
<211> LENGTH: 38
<212> TYPE: PRT
<213> ORGANISM: Camelus Linnaeus

<400> SEQUENCE: 3

Ser Tyr Ala Asp Ser Val Lys Gly Arg Phe Thr Ile Phe Lys Asp Asn
1               5                   10                  15

Ala Lys Asn Thr Leu Tyr Leu Asp Met Asn Ser Leu Asn Thr Glu Asp
            20                  25                  30

Thr Ala Met Tyr Tyr Cys
        35

<210> SEQ ID NO 4
<211> LENGTH: 11
<212> TYPE: PRT
<213> ORGANISM: Camelus Linnaeus

<400> SEQUENCE: 4

Trp Gly Gln Gly Thr Gln Val Thr Val Ser Ser
1               5                   10

<210> SEQ ID NO 5
<211> LENGTH: 10
<212> TYPE: PRT
<213> ORGANISM: Camelus Linnaeus

<400> SEQUENCE: 5

Gly Ser Thr Tyr Leu Arg Phe Ser Met Gly
1               5                   10

<210> SEQ ID NO 6
<211> LENGTH: 7
<212> TYPE: PRT
<213> ORGANISM: Camelus Linnaeus

<400> SEQUENCE: 6

Ile Gly Gly Asp Gly Arg Thr
1               5

<210> SEQ ID NO 7

```
<211> LENGTH: 23
<212> TYPE: PRT
<213> ORGANISM: Camelus Linnaeus

<400> SEQUENCE: 7

Ala Ala Ala Val Leu Leu Asp Gly Ser Phe Ser Leu Leu Ala Pro Leu
1               5                   10                  15

Val Pro Tyr Lys Tyr Asp Tyr
            20

<210> SEQ ID NO 8
<211> LENGTH: 129
<212> TYPE: PRT
<213> ORGANISM: Camelus Linnaeus

<400> SEQUENCE: 8

Gln Val Gln Leu Gln Glu Ser Gly Gly Gly Ser Val Gln Ala Gly Gly
1               5                   10                  15

Ser Leu Arg Leu Ser Cys Val Ala Ser Gly Ser Thr Tyr Leu Arg Phe
            20                  25                  30

Ser Met Gly Trp Phe Arg Gln Val Pro Asp Lys Glu Arg Glu Gly Val
        35                  40                  45

Ala Ala Ile Gly Gly Asp Gly Arg Thr Ser Tyr Ala Asp Ser Val Lys
    50                  55                  60

Gly Arg Phe Thr Ile Phe Lys Asp Asn Ala Lys Asn Thr Leu Tyr Leu
65                  70                  75                  80

Asp Met Asn Ser Leu Asn Thr Glu Asp Thr Ala Met Tyr Tyr Cys Ala
                85                  90                  95

Ala Ala Val Leu Leu Asp Gly Ser Phe Ser Leu Leu Ala Pro Leu Val
            100                 105                 110

Pro Tyr Lys Tyr Asp Tyr Trp Gly Gln Gly Thr Gln Val Thr Val Ser
            115                 120                 125

Ser

<210> SEQ ID NO 9
<211> LENGTH: 387
<212> TYPE: DNA
<213> ORGANISM: Camelus Linnaeus

<400> SEQUENCE: 9
caggtgcagc tgcaggagtc tgggggaggc tcggtgcagg ctggagggtc tctgagactc      60
tcctgtgtag cctcagggtc cacctacctg cgcttctcca tgggctggtt ccgccaggtt     120
ccagataagg agcgcgaggg ggtcgcagct attggcggtg atggtaggac aagctacgca     180
gactccgtaa agggccgatt caccatcttc aaagacaacg ccaagaatac tctgtatctg     240
gacatgaaca gcctgaacac cgaggacact gccatgtact actgtgcggc agcggtactc     300
ctagatggta gcttctcgct cctggcccct cagtaccat ataagtatga ctactggggc     360
cagggggaccc aggtcaccgt ctcctca                                        387

<210> SEQ ID NO 10
<211> LENGTH: 25
<212> TYPE: PRT
<213> ORGANISM: artificial sequence
<220> FEATURE:
<223> OTHER INFORMATION: synthesized

<400> SEQUENCE: 10

Gln Val Gln Leu Gln Glu Ser Gly Gly Gly Leu Val Gln Pro Gly Gly
```

```
1               5                   10                  15
Ser Leu Arg Leu Ser Cys Ala Ala Ser
            20                  25
```

<210> SEQ ID NO 11
<211> LENGTH: 15
<212> TYPE: PRT
<213> ORGANISM: artificial sequence
<220> FEATURE:
<223> OTHER INFORMATION: synthesized

<400> SEQUENCE: 11

```
Trp Phe Arg Gln Val Pro Gly Lys Gly Leu Glu Gly Val Ala Ala
1               5                   10                  15
```

<210> SEQ ID NO 12
<211> LENGTH: 38
<212> TYPE: PRT
<213> ORGANISM: artificial sequence
<220> FEATURE:
<223> OTHER INFORMATION: synthesized

<400> SEQUENCE: 12

```
Ser Tyr Ala Asp Ser Val Lys Gly Arg Phe Thr Ile Ser Lys Asp Asn
1               5                   10                  15

Ser Lys Asn Thr Leu Tyr Leu Asp Met Asn Ser Leu Arg Ala Glu Asp
            20                  25                  30

Thr Ala Val Tyr Tyr Cys
            35
```

<210> SEQ ID NO 13
<211> LENGTH: 11
<212> TYPE: PRT
<213> ORGANISM: artificial sequence
<220> FEATURE:
<223> OTHER INFORMATION: synthesized

<400> SEQUENCE: 13

```
Trp Gly Gln Gly Thr Leu Val Thr Val Ser Ser
1               5                   10
```

<210> SEQ ID NO 14
<211> LENGTH: 129
<212> TYPE: PRT
<213> ORGANISM: artificial sequence
<220> FEATURE:
<223> OTHER INFORMATION: synthesized

<400> SEQUENCE: 14

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Tyr Leu Arg Phe
            20                  25                  30

Ser Met Gly Trp Phe Arg Gln Val Pro Gly Lys Gly Leu Glu Gly Val
        35                  40                  45

Ala Ala Ile Gly Gly Asp Gly Arg Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Asp Met Asn Ser Leu Arg Ala Glu Asp Thr Ala Val Tyr Tyr Cys Ala
                85                  90                  95

Ala Ala Val Leu Leu Asp Gly Ser Phe Ser Leu Leu Ala Pro Leu Val
```

```
              100                 105                 110
Pro Tyr Lys Tyr Asp Tyr Trp Gly Gln Gly Thr Leu Val Thr Val Ser
        115                 120                 125
Ser

<210> SEQ ID NO 15
<211> LENGTH: 387
<212> TYPE: DNA
<213> ORGANISM: artificial sequence
<220> FEATURE:
<223> OTHER INFORMATION: synthesized

<400> SEQUENCE: 15
caggtgcagc tgcaggagag cggcggcggc ctggtgcagc ccggcggcag cctgaggctg      60
agctgcgccg ccagcggcag cacctacctg aggttcagca tgggctggtt caggcaggtg     120
cccggcaagg gcctggaggg cgtggccgcc atcgcggcg acggcaggac cagctacgcc      180
gacagcgtga agggcaggtt caccatcagc aaggacaaca gcaagaacac cctgtacctg     240
gacatgaaca gcctgagggc cgaggacacc gccgtgtact actgcgccgc cgccgtgctg     300
ctggacggca gcttcagcct gctggccccc ctggtgccct acaagtacga ctactggggc     360
cagggcaccc tggtgaccgt gagcagc                                         387
```

ANTI-PD-1 NANO-ANTIBODY AND APPLICATION THEREOF

INCORPORATION OF SEQUENCE LISTING

This application contains a sequence listing submitted in Computer Readable Form (CRF). The CFR file containing the sequence listing entitled "PB4083070-SequenceListing", which was created on Mar. 14, 2019, and is 6,788 bytes in size. The information in the sequence listing is incorporated herein by reference in its entirety.

TECHNICAL FIELD

The present disclosure relates to the field of biomedical or biopharmaceutical technology, and more specifically to the nanobodies against Programmed death 1 protein or PD-1 and the amino acid sequences thereof.

BACKGROUND

Programmed cell death-1 (PD-1), also known as CD279 (differentiation cluster 279), is a protein encoded by the PDCD1 gene in humans. Programmed cell death protein 1 is a type I transmembrane protein having 268 amino acids. Its structure mainly includes extracellular immunoglobulin variable region (IgV)-like domain (amino acid position of 21-170), hydrophobic transmembrane Region (amino acid position of 171-191) and intracellular region (amino acid position of 192-288). The intracellular region includes the C-terminal and N-terminal amino acid residues, and contains two independent phosphorylation sites, namely immunoreceptor tyrosine based inhibitory motif (ITIM), and immunoreceptor tyrosine based switch motif (ITSM). PD-1 is a cell surface receptor belonging to the immunoglobulin superfamily and is mainly expressed on the surface of activated T lymphocytes, B lymphocytes and macrophages. PD-1 binds to two ligands, programmed cell death 1 ligand 1 (PD-L1, or B7-H1) and programmed cell death 1 ligand 2 (PD-L2, or B7-DC).

T cells in resting state do not express PD-1, and when T cells are activated, PD-1 expression is induced by downstream signal molecules recruited by TCR. Activation of T cells produces a variety of cytokines such as IL-2, TNF-α and IFN-γ. The production of IFN-γ can induce up-regulation of PD-1 expression. The binding of PD-1 to PD-L1 inhibits the proliferation of T cells and decreases activity of T cells. The normal organism utilizes the binding of inhibitory receptors and ligands to influence the differentiation, proliferation and activation of T cells, thereby reducing activation level of T cells so as to maintain a moderate immune response and reduce damage to normal tissues and organs. However, tumor cells can use these inhibitory immune checkpoints to escape the recognition, attack and killing effects of T cells so that the tumor cells can survive and proliferate. Studies have shown that the expression of PD-1 is highly upregulated in tumor infiltrating lymphocytes (TIL), such as in breast cancer, prostate cancer, ovarian cancer, melanoma, non-small cell lung cancer and liver cancer. At the same time, various types of tumor cells express PD-L1. PD-L2 is expressed on macrophages, DC cells, Th2 helper cells and some tumor cells. The induced expression or up-regulation of PD-1 and PD-L1/PD-L2 in tumor patients is closely related to tumor immunological evasion.

The use of monoclonal antibodies in treatment of tumor is a rapidly growing field. Undoubtedly, treatment of cancer with monoclonal antibody is a huge success, which allows us to go further with personalized treatment. To date, approximately 20 or more monoclonal antibodies have been approved by the FDA and successfully entered into the market. Most of them inhibit tumor cell proliferation and angiogenesis by binding transmembrane receptors or soluble ligands and then interfering with their signal transduction pathways. However, due to the large size of monoclonal antibodies (about 150 kDa), it causes limited tumor penetration and slow distribution. Compared with monoclonal antibodies, nanobody has small size, high thermal stability and good solubility, etc. Moreover, it is relatively easy to produce nanobody on a large scale and at a reasonable cost by using bacterial, yeast or mammalian cells. It is found in the analysis that the VHH sequence has high homology with the human VH gene family III sequence, which suggests that the nanobody has low immunogenicity. As for tumor therapy, nanobodies can be used to specifically target antigens of tumor cells or tumor vasculature, block their signaling pathways, and inhibit tumor growth. In addition, nanobodies can also be used to block the binding between inhibitory receptors and ligands, stimulating binding of activated receptors and ligands to restore or enhance the normal killing effect of effector T cells on tumors. Nanobodies have many advantages and will play a great role in the tumor immunotherapy. The present invention contemplates the use of nanobody technology to obtain PD-1 nanobodies that block the binding of PD-1 to PD-L1 for use in tumor immunotherapy.

SUMMARY OF DISCLOSURE

The present invention provides a humanized PD-1 nanobody and amino acid sequence thereof, and also provides a nucleotide sequence encoding the nanobody of the present invention, an expression vector and a host cell for expressing the nanobody of the present invention, and a method for producing the nanobody of the present invention.

In the first aspect of the present invention, it provides complementary determining regions (CDRs) of VHH chain of anti-PD-1 nanobody, which are consisting of CDR1 as shown in SEQ ID NO.: 5, CDR2 as shown in SEQ ID NO.: 6 and CDR3 as shown in SEQ ID NO.: 7.

In another preferred embodiment, the CDR1, CDR2 and CDR3 are separated by frame regions FR1, FR2, FR3, and FR4 of the VHH chain.

In the second aspect of the present invention, it provides a VHH chain of anti-PD-1 nanobodies, which comprises frame regions (FR) and the complementary determining regions (CDR) of the first aspect, and said frame regions
   (a) are consisting of FR1 as shown in SEQ ID NO.:1, FR2 as shown in SEQ ID NO.: 2, FR3 as shown in SEQ ID NO.: 3, and FR4 as shown in SEQ ID NO.: 4; or
   (b) is consisting of FR1 as shown in SEQ ID NO.:10, FR2 as shown in SEQ ID NO.: 11, FR3 as shown in SEQ ID NO.: 12, and FR4 as shown in SEQ ID NO.: 13.

In another preferred embodiment, the VHH chain of said anti-PD-1 nanobodies is as shown in SEQ ID NO.: 8 or 14.

In the third aspect of the present invention, it provides an anti-PD-1 nanobody, which is an anti-PD-1 nanobody against PD-1 epitope, and has a VHH chain as shown in the amino acid sequence of SEQ ID NO.: 8 or SEQ ID NO.: 14.

In the fourth aspect of the present invention, it provides a polynucleotide, which encodes a protein selected from the group consisting of the CDRs of VHH chain of the anti-PD-1 nanobodies in the first aspect of the present invention, VHH chain of the anti-PD-1 nanobodies in the second aspect of the present invention, and the anti-PD-1 nanobodies in the third aspect of the present invention.

In another preferred embodiment, said polynucleotide has a nucleotide sequence of SEQ ID NO.: 9 or 15.

In another preferred embodiment, said polynucleotide includes DNA or RNA.

In the fifth aspect of the present invention, it provides an expression vector, which comprises the polynucleotide in the fourth aspect of the present invention.

In the sixth aspect of the present invention, it provides a host cell, which comprises the expression vector in the fifth aspect of the present invention, or the polynucleotide in the fourth aspect of the present invention is integrated into genome of the host cell.

In another preferred embodiment, said host cell includes prokaryocyte or eukaryocyte.

In another preferred embodiment, said host cell is selected from the group consisting of E. coli. and yeast cells.

In the seventh aspect of the present invention, it provides a method for producing anti-PD-1 nanobodies comprising the steps of:

(a) culturing said host cell in the sixth aspect of the present invention under a condition suitable for producing nanobodies, thereby obtaining a culture containing said anti-PD-1 nanobodies; and (b) isolating or recovering said anti-PD-1 nanobodies from said culture.

In another preferred embodiment, said anti-PD-1 nanobody has an amino acid sequence of SEQ ID NO.: 8 or 14.

In the eighth aspect of the present invention, it provides an immunoconjugate, which comprises:

(a) the VHH chain of said anti-PD-1 nanobodies in the second aspect of the present invention, or said anti-PD-1 nanobodies in the third aspect of the present invention; and (b) a conjugating moiety selected from the group consisting of a detectable label, drug, toxin, cytokine, radionuclide, and enzyme.

In another preferred embodiment, said conjugating moiety is a drug or toxin.

In another preferred embodiment, said conjugating moiety is a detectable label.

In another preferred embodiment, said conjugate is selected from the group consisting of fluorescent or luminescent labels, radio labels, MM (magnetic resonance imaging) or CT (computed tomography) contrast agents, or enzymes that produce detectable products, radionuclides, biotoxins, cytokines (e.g., IL-2, etc.), antibodies, antibody Fc fragments, antibody scFv fragments, gold nanoparticles/nanorods, viral particles, liposomes, nanomagnetic particles, prodrug activating enzymes (e.g., DT-diaphorase (DTD) or biphenyl hydrolase-like protein (BPHL)), chemotherapeutic agents (e.g., cisplatin) or any form of nanoparticles, etc.

In another preferred embodiment, said immunoconjugate contains multivalent (such as bivalent) VHH chains of the anti-PD-1 nanobodies in the second aspect of the present invention, or the anti-PD-1 nanobodies in the third aspect of the present invention.

In another preferred embodiment, said multivalent refers that the amino acid sequence of the immunoconjugate contains several repeated VHH chains of the anti-PD-1 nanobodies in the second aspect of the present invention, or the anti-PD-1 nanobodies in the third aspect of the present invention.

In the ninth aspect of the present invention, it provides a use of the anti-PD-1 nanobodies in the third aspect of the present invention for preparing (a) an agent for detecting PD-1 molecule; or (b) a medicine for treating cancers.

In another preferred embodiment, said detecting comprises detection conducted by flow cytometry or cell immunofluorescence.

In the tenth aspect of the present invention, it provides a pharmaceutical composition comprising:

(i) the complementary determining regions (CDRs) of VHH chain of the anti-PD-1 nanobodies in the first aspect of the present invention, the VHH chain of the anti-PD-1 nanobodies in the second aspect of the present invention, the anti-PD-1 nanobodies in the third aspect of the present invention, or the immunoconjugate in eighth aspect of the present invention; and (ii) a pharmaceutically acceptable carrier.

In another preferred embodiment, said pharmaceutical composition is in a form of injection.

In another preferred embodiment, said pharmaceutical composition is used for preparing a medicine for treating cancers, and said cancer is selected from the group consisting of gastric cancer, liver cancer, leukemia, renal tumor, lung cancer, small intestinal cancer, bone cancer, prostate cancer, colorectal cancer, breast cancer, colon cancer, prostate cancer, cervical cancer, lymphoma, adrenal tumor and bladder tumor.

In the eleventh aspect of the present invention, it provides one or more uses of the anti-PD-1 nanobodies in the third aspect of the present invention:

(i) for detecting human PD-1 molecule;
(ii) for flow cytometry assay;
(iii) for cell immunofluorescence detection;
(iv) for treating cancer; and
(v) for diagnosing cancer.

In another preferred embodiment, said use is non-diagnostic and non-therapeutic.

In the twelfth aspect of the present invention, it provides a recombinant protein which comprises:

(i) the sequence of variable region of heavy chain VHH in the second aspect of the present invention or the sequence of nanobodies in the third aspect of the present invention; and (ii) an optional tag sequence assisting expression and/or purification.

In another preferred embodiment, said tag sequence comprises 6His tag or HA tag.

In another preferred embodiment, said recombinant protein specifically binds to the PD-1 protein.

In the thirteenth aspect of the present invention, it provides a use of the VHH chain of the anti-PD-1 nanobodies in the second aspect of the present invention, the anti-PD-1 nanobodies in the third aspect of the present invention, or the immunoconjugate in eighth aspect of the present invention for preparing a medicine, agent, a detecting plate or a kit;

wherein, said agent, detecting plate or kit is used for detecting PD-1 protein in the testing sample;

wherein, said medicine is used for treating or preventing cancers expressing PD-1 (i.e., PD-1 positive).

In another preferred embodiment, said cancer comprises gastric cancer, lymphoma, liver cancer, leukemia, renal tumor, lung cancer, small intestinal cancer, bone cancer, prostate cancer, colorectal cancer, breast cancer, colon cancer, prostate cancer, or adrenal tumors.

In the fourteenth aspect of the present invention, it provides a method for detecting PD-1 protein in a sample which comprises the steps of:

(1) contacting the sample with the nanobodies in the third aspect of the present invention;

(2) detecting the antigen-antibody complex, wherein the detected complex indicates the presence of PD-1 protein.

In the fifteenth aspect of the present invention, it provides a method for treating a disease which comprises administering the nanobodies in the third aspect of the present invention or the immunoconjugate in the eighth aspect of the present invention to a subject in need.

In another preferred embodiment, said subject includes mammals, such as human.

In the sixteenth aspect of the present invention, it provides frame regions (FRs) of a VHH chain of an anti-PD-1 nanobody which are composed of FR1 as shown in SEQ ID NO.: 1, FR2 as shown in SEQ ID NO.: 2, FR3 as shown in SEQ ID NO.: 3, and FR4 as shown in SEQ ID NO.: 4.

It is to be understood that within the scope of the present invention, the above-described technical features of the present invention and the technical features specifically described in the following (e.g., examples) may be combined with each other to form a new or preferred technical solution, which will not be repeated herein due to the limited space.

DETAILED DESCRIPTION

Figure 1:
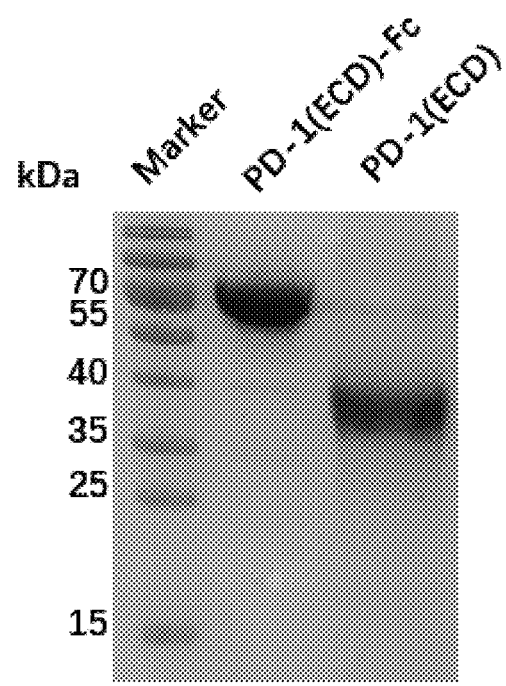
FIG. 1 shows the SDS-PAGE result of the purified antigen protein and nanobody, wherein the bands from left to right are the nucleic acid molecule for reference, the purified PD-1(ECD)-Fc protein, and the purified PD-1(ECD)-Fc protein after the Fc tag was removed by TEV enzyme. All of the above proteins were expressed by HEK293F cells. The purified antigen had a purity of more than 90% and could be used for subsequent camel immunization and screening for PD-1 nanobodies.

Upon extensive and intensive studies, the inventors have successfully obtained a class of anti-PD-1 nanobodies after numerous screening. The experimental results show that the anti-PD-1 nanobodies of the invention can effectively block the interaction between PD-L1 and PD-1.

Surprisingly, the humanized anti-PD-1 nanobodies of the invention can even more effectively block the binding between PD-L1 and PD-1. The characterization results show that the humanized anti-PD-1 nanobodies have high affinity, do not cross-react with other members in the PD-1 family. Based on this discovery, the invention is completed.

In particular, the human PD-1 protein as antigen was used to immunize a camel, thereby obtaining a gene library of nanobodies with high quality. The PD-1 protein molecules were conjugated onto an ESLIA plate and exhibited correct spatial structure of PD-1 protein. The antigens in such configuration were used to screen the gene library of nanobodies by phage exhibition technology (phage exhibition of a gene library of camel heavy chain antibody) thereby obtaining genes of nanobodies with PD-1 specificity. Then the genes were transferred into *E. coli* thereby obtaining nanobody stains which can be effectively expressed in *E. coli* with high specificity.

Terms

As used herein, the terms "nanobody of the invention", "anti-PD-1 nanobody of the invention", and "PD-1 nanobody of the present invention" are exchangeable and refer to nanobodies that specifically recognize and bind to PD-1 (including human PD-1). The more preferable nanobody is one comprising a VHH chain of amino acid sequence as shown in SEQ ID NO.:8 or 14.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end. The constant region of the light chain is corresponding to the first constant region of the heavy chain, and the variable region of the light chain is corresponding to the variable region of the heavy chain. Special amino acid residues form an interface between the variable regions of the light and heavy chains.

As used herein, the terms "single domain antibody (VHH)" and "nanobody" have the same meaning referring to a variable region of a heavy chain of an cloned antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained, the variable regions of the heavy chain of the antibody are therefore cloned so as to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-fold configuration, joined by three CDRs which form a linking loop, and in some cases can form a partially β-fold structure. The CDRs in each chain are closely adjacent to the others by the FR regions and form an antigen-binding site of the antibody with the CDRs of the other chain (see Kabat et al., NIH Publ. No. 91-3242, Volume I, pages 647-669. (1991)). The constant regions are not directly involved in the binding of the antibody to the antigen, but they exhibit different effector functions, for example, involve in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface label or an antigen that binds to said anti-PD-1 protein nanobody or the fragment thereof.

As used herein, the term "heavy chain variable region" and "VH" can be used interchangeably.

As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to PD-1 protein. They may or may not contain a starting methionine.

PD-1 Nanobodies

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure are spatially close to each other through the β-fold formed by the FRs therebetween. The CDRs on the heavy chain and the CDRs on the corresponding light chain constitute the antigen-binding site of the antibody. The amino acid sequences of the same type of antibodies can be compared to determine which amino acids constitute the FR or CDR regions.

The variable regions of the heavy chains of the antibodies of the invention become a particular interest because at least a part of them is involved in binding antigens. Thus, the present invention includes those molecules having an antibody heavy chain variable region with CDRs, provided that their CDRs are 90% or more (preferably 95% or more, the most preferably 98% or more) identical to the CDRs identified herein.

The present invention includes not only intact antibodies but also fragments of antibody or fusion proteins formed by the antibodies with other sequences, which are immunologically active. Therefore, the present invention also includes fragments, derivatives and analogs of the antibody.

As used herein, the terms "fragment," "derivative," and "analog" refer to a polypeptide that substantially retains the same biological function or activity of an antibody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6His tag). According to the teachings herein, these fragments, derivatives, and analogs are within the scope of one of ordinary skill in the art.

The antibody of the present invention refers to a polypeptide including the above CDR regions having PD-1 protein binding activity. The term also encompasses variant forms of polypeptides comprising the above CDR regions that have the same function as the antibodies of the invention. These variations include, but are not limited to, deletion, insertion and/or substitution of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the antibodies of the invention.

The variant forms of the polypeptide include: homologous sequences, conservative variants, allelic variants, natural mutants, induced mutants, proteins encoded by DNAs capable of hybridizing with DNA encoding the antibody of the present invention under high or low stringent conditions, and polypeptides or proteins obtained using antiserum against the antibodies of the invention.

The invention also provides other polypeptides, such as a fusion protein comprising antibodies or fragments thereof. In addition to almost full-length polypeptides, the present invention also includes fragments of the antibodies of the invention. Typically, the fragment has at least about 50 contiguous amino acids of the antibody of the invention, preferably at least about 50 contiguous amino acids, more preferably at least about 80 contiguous amino acids, and most preferably at least about 100 contiguous amino acids.

In the present invention, "a conservative variant of an antibody of the present invention" refers to the polypeptides in which there are up to 10, preferably up to 8, more preferably up to 5, and most preferably up to 3 amino acids substituted by amino acids having analogical or similar properties, compared to the amino acid sequence of the antibody of the present invention. These conservative variant polypeptides are preferably produced according to the amino acid substitutions in Table 1.

TABLE 1

| Original residue | Representative substitution | Preferable substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above antibody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only when the identity between the two sequences is at least over 90%, preferably over 95%. Also, polypeptides encoded by hybridizable polynucleotides have the same biological functions and activities as mature polypeptides.

The full-length nucleotide sequence of the antibody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then ligating them. In addition, the coding sequence of the heavy chain and the expression tag (e.g., 6His) can be fused together to form a fusion protein.

Once the concerned sequences are obtained, the sequences of interest can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*, bacterial cells such as *Salmonella typhimurium*, fungal cells such as yeast, insect cells of *Drosophila* S2 or Sf9, animal cells of CHO, COST, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$) method. The procedures used are well known in the art. Another method is to use MgCl₂. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods by utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultracentrifugation, molecular sieve chromatography (gel filtration), adsorption layer analysis, ion exchange chromatography, high performance liquid chromatography (HPLC), and various other liquid chromatography techniques and the combinations thereof.

The antibodies of the invention may be used alone or in combination or conjugated with a detectable label (for diagnostic purposes), a therapeutic agent, a PK (protein kinase) modification moiety, or any combination thereof.

Detectable labels for diagnostic purposes include, but are not limited to: fluorescent or luminescent markers, radioactive markers, Mill (magnetic resonance imaging) or CT (computed tomography) contrast agents, or enzymes capable of producing detectable products.

Therapeutic agents that can be bound or conjugated to the antibodies of the present invention include, but are not limited to: 1. radionuclides; 2. biological poisons; 3. cytokines such as IL-2, etc.; 4. gold nanoparticles/nanorods; 5. viruses particles; 6. liposome; 7. nano magnetic particles; 8. prodrug activating enzymes (for example, DT-diaphorase (DTD) or biphenyl hydrolase-like protein (BPHL)); 10. chemotherapeutic agents (for example, cisplatin) or any form of nanoparticles, etc.

TABLE 2

Nanobody before and after humanization in the invention

| No. of SEQ | Nanobody before humanization No. | Nanobody after humanization No. |
|---|---|---|
| FR1 sequence | SEQ ID NO: 1 | SEQ ID NO: 10 |
| FR2 sequence | SEQ ID NO: 2 | SEQ ID NO: 11 |
| FR3 sequence | SEQ ID NO: 3 | SEQ ID NO: 12 |
| FR4 sequence | SEQ ID NO: 4 | SEQ ID NO: 13 |
| CDR1 sequence | SEQ ID NO: 5 | SEQ ID NO: 5 |
| CDR2 sequence | SEQ ID NO: 6 | SEQ ID NO: 6 |
| CDR3 sequence | SEQ ID NO: 7 | SEQ ID NO: 7 |
| amino acid sequence | SEQ ID NO: 8 | SEQ ID NO: 14 |
| nucleotide sequence | SEQ ID NO: 9 | SEQ ID NO: 15 |

Pharmaceutical Composition

The invention also provides a composition. Preferably, said composition is a pharmaceutical composition comprising the above antibody or active fragment or fusion protein thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind PD-1 protein molecule and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned antibodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of an injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 micrograms/kilogram body weight to about 50 milligrams/kilogram body weight per day. In addition, the polypeptides of the invention can also be used with other therapeutic agents.

When a pharmaceutical composition is used, a safe and effective amount of the immunoconjugate is administered to the mammal, wherein the safe and effective amount is usually at least about 10 micrograms/kilogram body weight, and in most cases, no more than about 50 mg/kilogram body weight, preferably the dose is about 10 micrograms/kilogram body weight to about 10 milligrams/kilogram body weight. Of course, factors such as the route of administration and the patient's health status should be considered to define the specific doses, all of which are within the skills of skilled physicians.

Nanobodies with Labels

In a preferred embodiment of the invention, the nanobodies carry detectable labels. More preferably, the label is selected from the group consisting of isotopes, colloidal gold labels, colored labels, and fluorescent labels.

Colloidal gold labels can be prepared using methods known to those skilled in the art. In a preferred embodiment of the invention, the anti-PD-1 nanobodies are marked with colloidal gold to obtain colloidal gold-labeled nanobodies.

The anti-PD-1 nanobodies of the present invention have very good specificity and high potency.

Detection Method

The invention also relates to a method of detecting PD-1 protein. The method steps are basically as follows: obtaining a sample of cells and/or tissue; dissolving the sample in a medium; and detecting the level of PD-1 protein in the dissolved sample.

According to the detection method of the present invention, the sample used is not particularly limited, and a representative example is a sample containing cells which is present in a cell preservation solution.

Kits

The present invention also provides a kit containing an antibody (or a fragment thereof) or a detection board of the present invention. In a preferred embodiment of the present invention, the kit further includes a container, an instruction, a buffer, and the like.

The present invention also provides a detection kit for detecting the level of PD-1, and said kit comprises antibodies that recognize PD-1 protein, a lysis medium for dissolving a sample, a general reagent and a buffer needed for the detection, such as various buffers, detection labels, detection substrates, etc. The test kit can be an in vitro diagnostic device.

Application

As described above, the nanobodies of the present invention have extensive biological application value and clinical application value. Said applications involve various fields such as diagnosis and treatment of diseases related to PD-1, basic medical research, and biological research. One preferred application is for clinical diagnosis and treatment targeting PD-1.

The main advantages of the present invention include:

(a) the nanobodies of the invention highly specifically bind human PD-1 protein with a correct spatial structure;

(b) the nanobodies of the invention have a strong affinity; and (c) the nanobodies of the invention does not cross-react with other members of the PD-1 family, and has a high specificity.

The present invention is further described in combination with specific embodiments. It should be understood that these examples are only for illustrating the present invention and are not intended to limit the scope of the present invention. The experimental methods that do not specify the specific conditions in the following examples are generally performed according to conventional conditions such as those described in Sambrook et al., Molecular Cloning: A Laboratory Manual (New York: Cold Spring Harbor Laboratory Press, 1989), or according to the conditions recommended by the manufacturer. Unless otherwise indicated, percentages and parts are percentages by weight and parts by weight.

Example 1: Expression and Purification of Human PD-1 Protein (1) Firstly, the amino acid sequence and nucleotide sequence of human PD-1 were searched from UniProt, and the full-length nucleic acid sequence of PD-1 was integrated into pCDNA3.1(−) vector by the company, and the sequence of the extracellular domain was sub-cloned into pFUSE-IgG1 vector (commercially available from Invitrogen), wherein a TEV cleavage site and a GS linker were introduced at the end of the extracellular domain of PD-1 for later excision of the tag to obtain the Fc-free PD-1 (ECD) protein;

(2) An Omega plasmid maxi kit was used to extract the constructed pFUSE-PD-1(ECD)-hIgG1-Fc2 plasmid;

(3) HEK293F cells were cultured until an OD reached $2.0 \times 10^6$ cells/mL;

(4) The plasmid and the transfection agent PEI were mixed (1:3) well and placed in transfection medium F17 (Gibco) for 20 min, and then the product was added into HEK293F cells culture for further incubation in a shaker under 6% $CO_2$ at 37° C. for 6 days;

(5) The supernatant of the cells was collected and subjected to binding with Protein A beads at room temperature for 1 hour;

(6) After the beads were washed by PBS (pH 7.0), 0.1 M of Glycine (pH3.0) was used to elute the PD-1(ECD) protein with Fc-tag.;

(7) The eluted proteins were ultrafiltrated into PBS and sampled for an SDS-PAGE test after yield measurement;

(8) The expressed PD-1(ECD)-Fc protein was cleavaged by using 0.2 mg TEV enzyme per 1 mg PD-1(ECD)-Fc protein at 4° C. for 16 hours. The protein solution was loaded onto a Ni column and a Protein A column subsequentially and the flow-through was collected and sampled to an SDS-PAGE test to detect the excision of Fc-tag. The results of SDS-PAGE electrophoresis before and after PD-1 (ECD)-Fc protein TEV digestion were shown in FIG. 1.

The results of electrophoresis showed that the antigen PD-1 (ECD) prepared by this method has a high purity and was suitable for subsequent camel immunization and screening for PD-1 Nanobody.

Example 2: The Construction of PD-1 Nanobody Library (1) 1 mg of PD-1 (ECD) antigen was mixed with Freund's adjuvant in equal volume to immunize a Xinjiang bactrian camel once a week for a total of 7 times to stimulate B cells to express antigen-specific PD-1(ECD) nanobodies;

(2) After the 7 immunizations were completed, 100 mL of camel peripheral blood lymphocytes were sampled and total RNA was extracted.

(3) cDNA was synthesized and VHH was amplified using reverse PCR;

(4) Phage display vector and VHH were digested with restriction endonucleases PstI and NotI, and the enzyme-cut VHH fragments were then ligated into the vector at a certain molar ratio at 16° C. for 16 h.

(5) The ligated product was electronically transfected into competent TG1 cells, and the phage display library of the PD-1 nanobody was constructed and the capacity thereof was determined.

Figure 2:
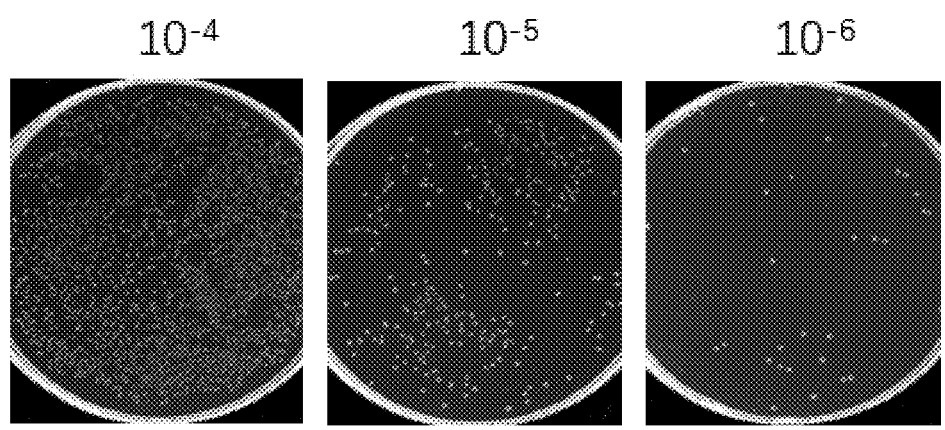
FIG. 2 shows the detection result for the library capacity of the constructed library. The constructed library was coated onto a plate after being serially diluted. The figure shows ⅕ of the clones with gradient dilution of $10^4$ fold, $10^5$ fold, and $10^6$ fold, and the number of clones was counted to be $2.3 \times 10^9$ CFU indicating the capacity of the library was large.
Figure 3:
FIG. 3 shows detection result for the insertion rate of the constructed nanobody library. The DNA bands in the gel pores from left to right respectively correspond to DNA molecule marker (the first lane), and PCR products of detected insertion fragment (in the other lanes). The PCR product lane was about 500 bp. The insertion rate as detected was up to 100%. It indicated that the constructed library was of high quality.

After detection, the library had a storage capacity of $2.3 \times 10^9$ CFU (as shown in FIG. 2), and the correct insertion rate of the VHH fragment was 100%. FIG. 3 shows the correct insertion of the VHH fragment by colony PCR, indicating the constructed phage display library had a high quality and could be used for screening nanobodies against PD-1.

Example 3: Screening and Verification of PD-1 Nanobodies

Figure 4:
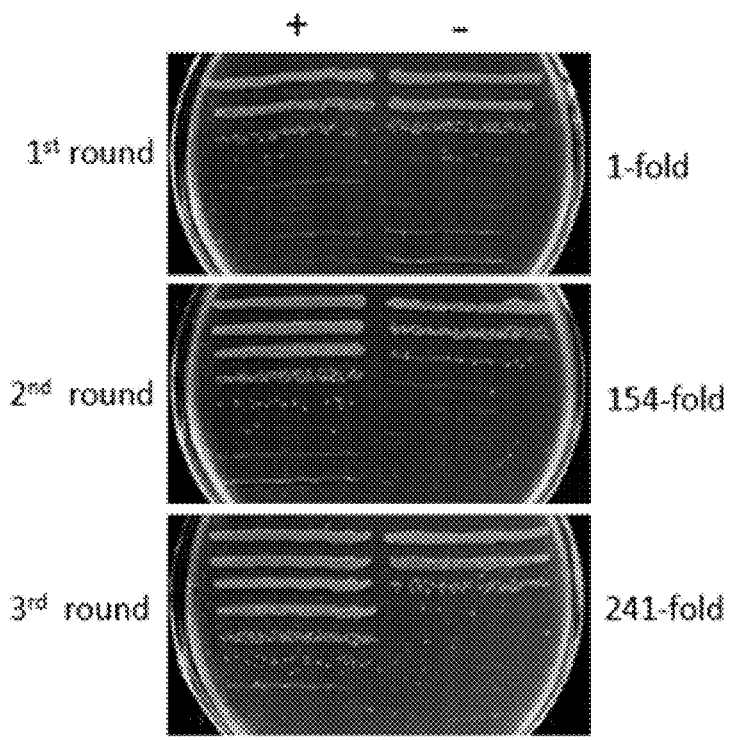
FIG. 4 shows the screening and enrichment process of PD-1 nanobodies. There was no enrichment after the first round of panning. It was a 154-fold enrichment after the second round of panning and a 241-fold enrichment after the third round of panning. The increasing enrichment factor indicated that the nanobodies against PD-1 were enriched.
Figure 5:
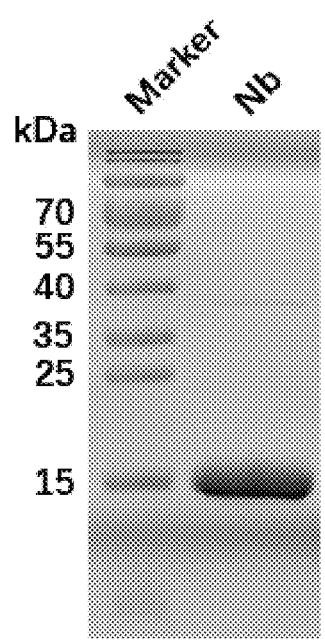
FIG. 5 shows the illustration of purified PD-1 nanobodies (corresponding to the nanobody of the amino acid of SEQ ID NO.: 8) expressed by *E. coli*. It was an SDS-PAGE electrophoretogram of PD-1 nanobody upon the Ni-column affinity chromatography purification. The results indicated that the purity of PD-1 was over 90% after purification and such a good purity was suitable for subsequent experiments.

Screening of Nanobodies (1) 10 μg PD-1 (ECD) antigens dissolved in 100 mM $NaHCO_3$ (pH 8.2) was added onto the NUNC ELISA plate and left overnight at 4° C. for coating;

(2) The next morning, the antigen solution in the well was aspirated, washed with PBST (0.05% PBS+Tween-20) for 5 times, then 100 μl of 0.1% BSA was added, and blocked at room temperature for 2 h;

(3) After 2 h, phages ($2 \times 10^{11}$ CFM of phage display gene library with nanobodies of immunized camel) were added and reacted at room temperature for 1 h;

(4) Wash 5 times with PBST, to wash off phage display nanobodies that did not bind to antigen PD-1 (ECD);

(5) The phages specifically bound to PD-1 were dissociated by 100 mM triethanolamine, and *E. coli* TG1 cells in logarithmic phase were infected and incubated at 37° C. for 1 h. The phages were generated and purified for the next round of screening. The screening process was repeated for 3 rounds. The enrichment results were shown in FIG. 4.

Screening specific single positive clones by using phage-based enzyme-linked immunosorbent assay (ELISA):

(1) From the cell culture dishes containing bacteriophages obtained in the above 2-3 rounds of screening, 96 single colonies were picked and inoculated in TB medium containing 100 μg/mL ampicillin (12.52 g $K_2HPO_4$, 2.3 g $KH_2PO_4$, 24 g yeast extract, 12 g peptone, 4 mL glycerol in 1 liter ddH20). When the OD of the bacterial solution reached 0.6-0.9, 1M IPTG was added in a ratio of 1000:1, and the expression was induced at 28° C. for 16 h.

(2) Crude nanobodies were obtained by osmotic method, and the nanobodies were transferred into an antigen-coated ELISA plate and allowed to place at 37° C. for 1 hour.

(3) The plate was washed with PBST (×5) to remove unbound nanobodies and other impurities and the primary antibody (anti-mouse anti-HA nanobody, purchased from Beijing Kangwei Century Biotechnology Co., Ltd.) was added. The mixture was placed at 37° C. for 1 hour.

(4) Unbound primary antibodies were washed away with PBST, and the secondary antibody (alkaline phosphatase-labeled goat anti-mouse antibody) was added. The mixture was placed at 37° C. for 0.5 hour.

(5) The plate were washed with PBST (×5), and alkaline phosphatase staining solution was added. The absorbance was read at 405 nm on an ELISA instrument.

(6) When OD value of the sample well was over 3 times of the OD value of the control well, it is confirmed as a positive clone.

(7) The bacteria in the positive clone wells were shaken in an LB liquid (adding a stock solution containing 100 μg/mL ampicillin in a ratio of 1000:1) for plasmid extraction and sequencing.

(8) Amino acid sequence alignment analysis was performed on the sequencing results, and a nanobody having differences in CDR1, CDR2 or CDR3 region was regarded as one strain.

Example 4: Flow Cytometry High-Throughput Screening of Nanobodies with Blocking Effects (1) Different clones with the correct sequencing were inoculated into 1 ml of TB medium containing 100 μg/ml ampicillin, and incubated at 37° C. in a constant temperature shaker. IPTG inducer was added during the logarithmic growth phase to a final concentration of 1 mM and expression was induced at 28° C. for 16 h;

(2) After 16 hours, the cells were disrupted by osmotic pressure to obtain a crude nanobody extract;

(3) hPD-1-Fc-biotin proteins were prepared (The preparation method for hPD-1-Fc was identical to that in Example 1). The biotinylation of the protein was conducted according to the biotin reagent instructions;

(4) For each sample, 1×10$^6$ HEK293F cells transiently transfected to express human PD-1 full-length protein were taken and resuspended in 0.5% BSA-PBS buffer, and 200 μl of the above-mentioned PD-1 crude nanobody extract was added. Nivolumab was set as a positive control and AF70 Nb was set as a negative control. 5 μg of hPD-1-Fc-biotin was added into each of the samples and subjected to incubation at 4° C. for 20 min.

(5) The cells were washed twice with PBS, and SA-PE (purchased from eBioscience) was added. The mixture was incubated at 4° C. for 20 minutes. A flow cytometry (BD FACS Calibur) was used for determine the cells after they were washed twice with PBS. A PD-1 nanobody with a good blocking effect was initially screened out.

Example 5: Expression of Nanobodies in *E. coli* Host and Purification (1) The plasmid of initially screened nanobody with good blocking effect was electro-transformed into *E. coli* WK6, which then coated onto LA+Glucose (a culture plate containing ampicillin and glucose) for incubation overnight at 37° C.;

(2) A single colony was picked, inoculated into 5 mL LB culture medium which contained ampicillin, and cultured in a shaker overnight at 37° C.;

(3) 1 mL overnight-cultured strain fluid was inoculated into 330 mL TB medium and cultured in a shaker at 37° C. to an OD value of 0.6-0.9. IPTG was added to a final concentration of 1 mM and expression was induced at 28° C. for 16 h;

(4) The strains were collected by centrifuged at 8000 rpm at 4° C.;

(5) The bacteria was disrupted by osmotic pressure shock method, the nanobody was released, and the supernatant was centrifuged to obtain a crude nanobody extract;

(6) The His-tag nanobody was purified by Ni column affinity chromatography. The results of SDS-PAGE showed that the purity of PD-1 nanobody was over 90% after the purification process, and was suitable for subsequent experiments.

Example 6: Blocking Effect of Nanobodies Tested by Flow Cytometry (1) For each sample, 1×10$^6$ HEK293F cells transiently transfected to express human PD-1 full-length protein were taken and resuspended in 0.5% BSA-PBS buffer, and 10 μg of the above-mentioned purified PD-1 nanobody was added. Nivolumab was set as a positive control and AF70 Nb was set as a negative control. 5 μg of hPD-1-Fc-biotin was added into each of the samples and subjected to incubation at 4° C. for 20 min.

Figure 6:
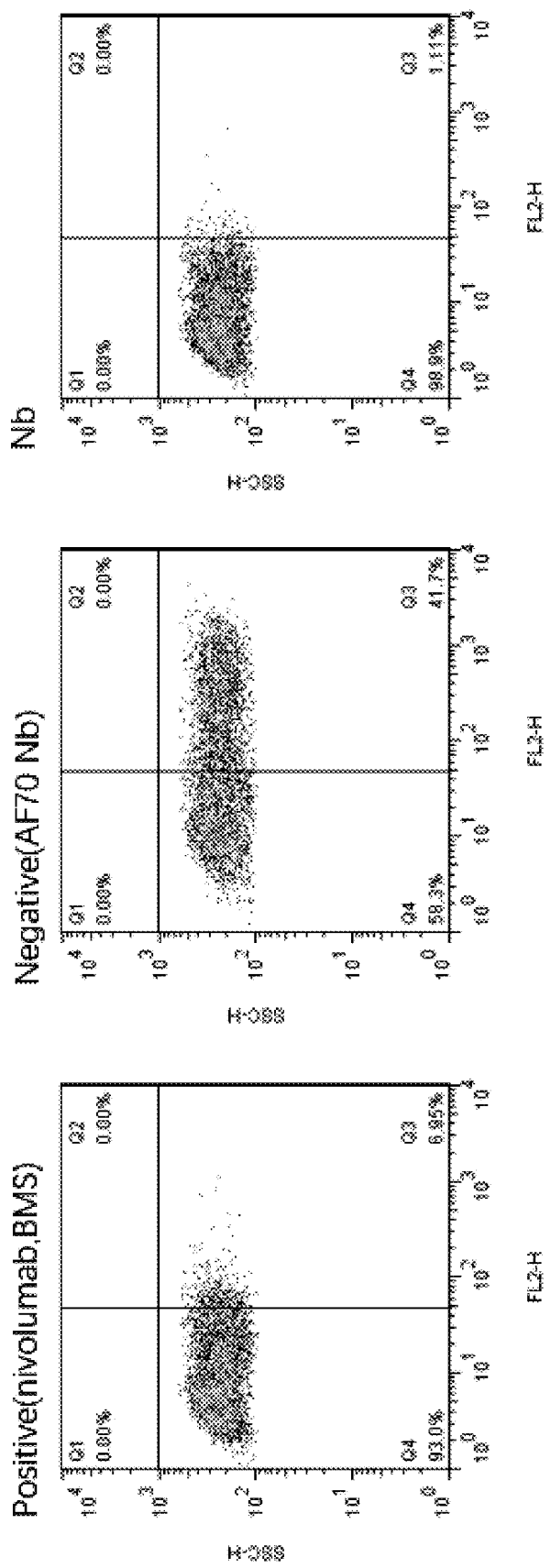
FIG. 6 shows the blocking effects of PD-1 nanobodies tested by FACS. It is conducted by the co-reaction of HEK293F cells transient transfected to express human full-length PD-1 protein, various nanobodies and biotinylated hPD-L1-Fc protein. The results showed that this strain of nanobody had a good effect of blocking the binding of PD-1 to its ligand PD-L.

(2) The cells were washed twice with PBS, and SA-PE (purchased from eBioscience) was added. The mixture was incubated at 4° C. for 20 minutes. A flow cytometry (BD FACS Calibur) was used for determine the cells after they were washed twice with 1×PBS. The determination results were shown in FIG. 6. The results of flow cytometry showed that the prokaryotic expression of this antibody had a good effect on blocking the binding of PD-1 to its ligand PD-1, and its blocking effect was better than that of commercial PD-1 monoclonal antibody (Nivolumab, BMS) under the same molecular mass.

Example 7: Humanization of PD-1 Nanobodies (1) Firstly, the PD-1 nanobody sequence of SEQ ID NO.: 8 was used as a template to search for homologous structures in the structural database, wherein 12 structures were taken (E value=0.0, and sequence identity ≥70%);

(2) These 12 structures were subjected to structural comparison. Based on the resolution of the crystal structure and the constructed evolutionary tree, 9 proteins including 3 dwt were finally selected for multi-template homology modeling based on the PD-1 nanobody sequence of SEQ ID NO.: 8. Finally, 5 structures were obtained. The structures with lowest molpdf were selected according to the ranking of the scoring function from top to bottom and then used for the further process.

(3) For those best structures obtained from modeling, the solvent accessibility of the residues was calculated by ProtSA server (i.e. the ratio of the solvent contactable surface of the residues between folding and un-folding state). The residues with a value over 40% were taken as the residues exposed to the solvent.

(4) An alignment was conducted between the best structures obtained from modeling and DP-47 sequence and the corresponding residues exposed to the solvent were substituted. The humanized PD-1 nanobodies of the amino acid sequence as set forth in SEQ ID NO:10 and SEQ ID NO.: 14 were ultimately determined. The comparison of the identity between the nanobody framework region and the DP-47 framework region before and after humanization was shown as below:

| FR structure | Identity with DP-47 before humanization | Identity with DP-47 after humanization |
|---|---|---|
| FR1 | 80% | 92% |
| FR2 | 53.3% | 73.3% |
| FR3 | 78.9% | 92.1% |
| FR4 | 90.9% | 100% |

Figure 7:
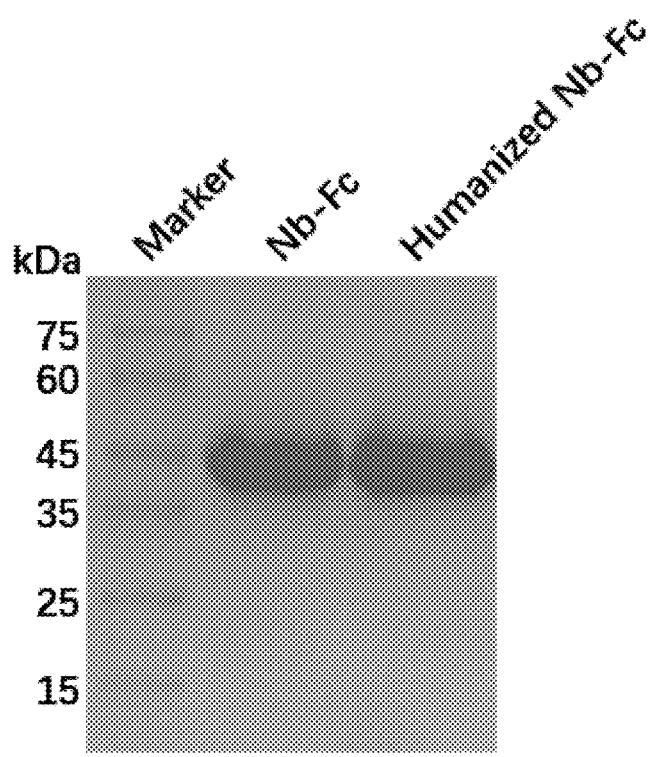
FIG. 7 illustrates the purification of the non-humanized and humanized PD-1 nanobodies which were eukaryotically expressed. The humanized PD-1 nanobodies were expressed by HEK293F cells, wherein the bands from left to right were the protein molecule as a standard, the PD-1 nanobody (before humanization) expressed by HEK293F cells, the PD-1 nanobody (after humanization) expressed by HEK293F cells. The expressed nanobody had an Fc-tag and the protein purity was over 90% indicating a good purity.

Example 8: Expression of Humanized PD-1 Nanobodies in Eukaryocyte HEK293 and Purification (1) The PD-1 nanobody (Nb) sequences before and after humanization were separately synthesized on pFUSE-hIgG1-Fc2 vector, transformed into *E. coli* DH5a strain and cultured in shaker, and the pFUSE-Nb-hIgG1-Fc2 plasmid was extracted using Omega plasmid maxi kit;

(2) HEK293F cells were cultured to an OD of $2.0 \times 10^6$ cells/mL;

(3) The filtrated and sterilized plasmid and the transfection reagent PEI (1:3) were mixed well and placed in transfection medium F17 for 20 min, and then the mixture was added to HEK293F cells, and cultured in a 6% $CO_2$ shaker at 37° C. for 5 days;

(4) The cell supernatant was collected and subjected to the binding with Protein A beads at room temperature for 1 hour;

(5) After washing the beads with phosphate buffer (pH 7.0), the PD-1(ECD)-Fc proteins before and after humanization were eluted with 0.1M Glycine pH 3.0;

(6) The eluted proteins were ultrafiltrated into PBS. SDS-PAGE electrophoresis was used to detect the Fc-tagged nanobody before and after humanization obtained via eukaryotic expression and purification. The results were shown in FIG. 7.

The results showed that the purity of Fc-tagged nanobodies after eukaryotic expression reached more than 90%, which indicated a high purity.

Example 9: Specificity of Purified Nanobody by ELISA (1) The humanized nanobody gene fragment was ligated into the pMECS vector, and the clone with the correct sequencing was transferred into the WK6 strain. The expression and purification were conducted, which were the same as those in Example 5);

(2) The antigen proteins PD-1 (human), PD-1 (monkey), PD-1 (mice), ICOS (human), CTLA-4 (human), CD28 (human), IgG1 (human) were coated overnight at 4° C. with 0.5 μg per well (5 μg/mL, 100 μL), and IgG1 was coated as a control.

(3) The plates were washed by PBST (×5) next day, and 200 μL 1% BSA was added to block in RT for 2 hours;

(4) Each biotinylated nanobody was diluted to 10 μg/mL, and 100 μL of each dilution was incubated in each well and allowed to react at 37° C. for 1 hour.

(5) The unbound nanobodies were washed with PBST, 100 μL of mouse anti-HA tag antibody was added and incubated at 37° C. for 1 hour;

(6) Unbound primary antibody was washed away by PBST (×5), and goat anti-mouse alkaline phosphatase conjugated antibody was added. The incubation was at 37° C. for 0.5 hour.

Figure 8:
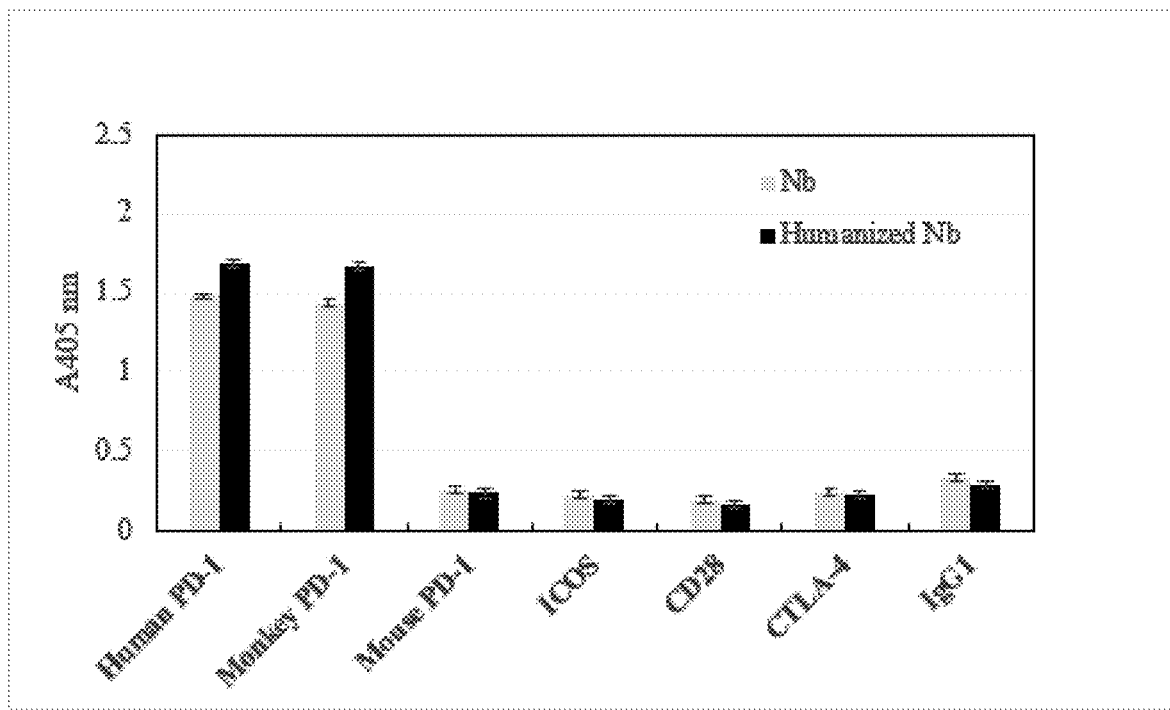
FIG. 8 shows the specificity results of PD-1 nanobodies tested by ELISA. It could be seen that the nanobody only interacted with the extracellular sections of human and monkey-derived PD-1 (Human and monkey PD-1 extracellular domain sequence have 100% identity), but did not cross-react with mouse PD-1 or other PD-1 family members. The results indicated the nanobody had good species specificity.

(7) Unbound secondary antibody was washed away by PBST (×5), and alkaline phosphatase staining solution was added. The absorbance was read at 405 nm on an ELISA instrument. The results were shown in FIG. 8.

The specificity of the nanobody was determined based on the absorbance. The results showed that the nanobody only interacted with the extracellular sections of human and monkey-derived PD-1 (human and monkey PD-1 extracellular domain sequences have 100% identity), but did not cross-react with mouse PD-1 or other PD-1 family members. The results indicated that the nanobody had good species specificity.

Example 10: Blocking Effect of the Humanized PD-1 Nanobodies Determined by Flow Cytometry The method was identical to that in Example 6:

(1) For each sample, $1 \times 10^6$ HEK293F cells transiently transfected to express human PD-1 full-length protein were taken from and resuspended in 0.5% BSA-PBS buffer, and 10 μg of the above-mentioned purified PD-1 nanobody was added. Nivolumab was set as a positive control and AF70 Nb was set as a negative control. 5 μg of hPD-1-Fc-biotin was added into each of the samples and subjected to incubation at 4° C. for 20 min.

Figure 9:
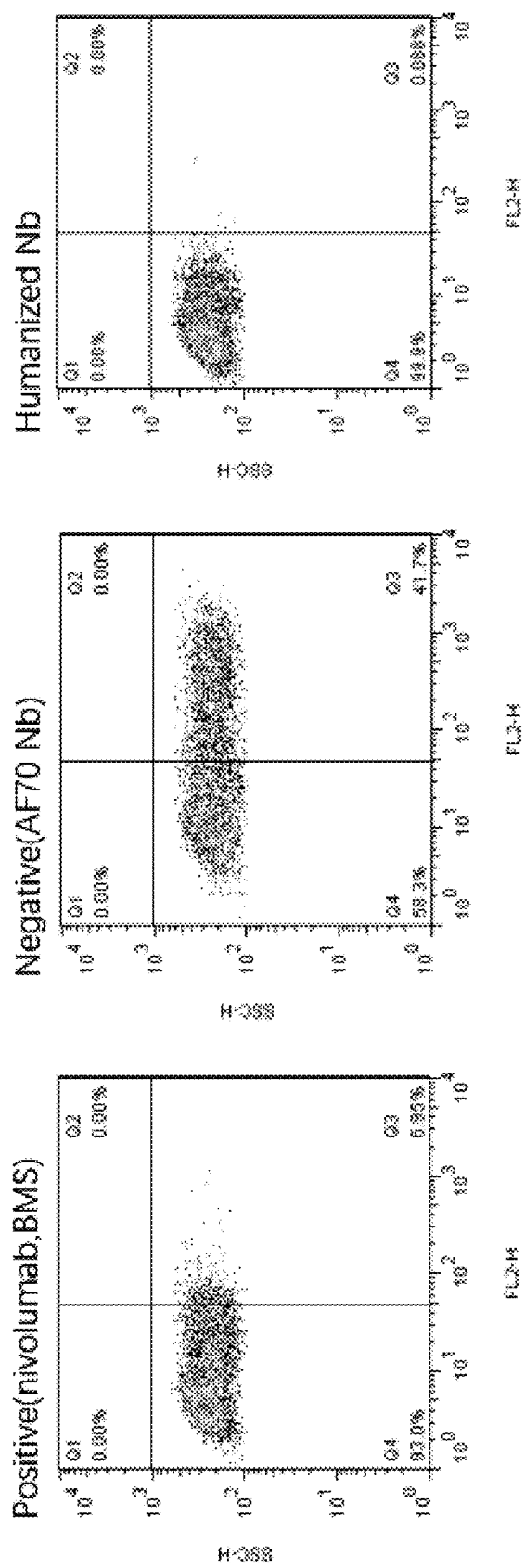
FIG. 9 shows the blocking effects of humanized PD-1 nanobodies tested by FACS. It is conducted by the co-reaction of HEK293F cells transient transfected to express human full-length PD-1 protein, various nanobodies and biotinylated hPD-L1-Fc protein. The results showed that this strain of nanobody had a good effect of blocking the binding of PD-1 to its ligand PD-L.

(2) The cells were washed twice with 1×PBS, and SA-PE (purchased from eBioscience) was added. The product was incubated at 4° C. for 20 minutes. A flow cytometry (BD FACS Calibur) was used for determine the cells after they were washed twice with 1×PBS. The determination results were shown in FIG. 9.

The results of flow cytometry showed that the humanized PD-1 nanobody still effectively blocked the binding of PD-1 to PD-L1.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

The invention claimed is:

1. An anti-PD-1 nanobody, wherein the anti-PD-1 nanobody comprises a VHH chain which has three complementary determining regions (CDRs): CDR1 as shown in SEQ ID No: 5, CDR2 as shown in SEQ ID No: 6 and CDR3 as shown in SEQ ID No: 7.

2. The anti-PD-1 nanobody of claim 1, which comprises frame regions (FRs) selected from the group consisting of
   (a) FR1 as shown in SEQ ID No: 1, FR2 as shown in SEQ ID No: 2, FR3 as shown in SEQ ID No: 3, and FR4 as shown in SEQ ID No: 4; and
   (b) FR1 as shown in SEQ ID No: 10, FR2 as shown in SEQ ID No: 11, FR3 as shown in SEQ ID No: 12, and FR4 as shown in SEQ ID No: 13.

3. The anti-PD-1 nanobody of claim 1, wherein the nanobody is against PD-1 epitope, and has a VHH chain as shown in the amino acid sequence of SEQ ID NO: 8 or SEQ ID NO: 14.

4. A polynucleotide which encodes the anti-PD-1 nanobody according to claim 1.

5. The polynucleotide according to claim 4, which has a nucleotide sequence of SEQ ID Nos: 9 or 15.

6. A method for producing an anti-PD-1 nanobody which comprises:
   (a) culturing a host cell under a condition suitable for producing nanobody, thereby obtaining a culture containing the anti-PD-1 nanobody, wherein the host cell contains an expression vector which contains the polynucleotide encoding anti-PD-1 nanobody of claim 1, or the polynucleotide is integrated in genome of the host cell; and
   (b) isolating or recovering the anti-PD-1 nanobody from the culture.

7. An immunoconjugate, which contains:
   (a) the anti-PD-1 nanobody according to claim 1; and
   (b) a moiety selected from the group consisting of a detectable label, drug, toxin, cytokine, radionuclide, and enzyme.

8. The immunoconjugate of claim 7, wherein the moiety is selected from the group consisting of fluorescent or luminescent labels, radio labels, MRI or CT contrast agents, enzymes that produce detectable products, radionuclides, biotoxins, cytokines, antibodies, antibody Fc fragments, antibody scFv fragments, gold nanoparticles or nanorods, viral particles, liposomes, nanomagnetic particles, prodrug activating enzymes, and chemotherapeutic agent.

9. A pharmaceutical composition which comprises:
   (i) the anti-PD-1 nanobody of claim 1, or an immunoconjugate containing said anti-PD-1 nanobody and a moiety selected from the group consisting of a detectable label, drug, toxin, cytokine, radionuclide, and enzyme; and
   (ii) a pharmaceutically acceptable carrier.

10. A method for treating a disease in a subject which comprises administering an anti-PD-1 nanobody of claim 1, or an immunoconjugate containing the anti-PD-1 nanobody and a conjugating moiety to a subject in need selected from the group consisting of a detectable label, drug, toxin, cytokine, and radionuclide;
    wherein the disease is a cancer selected from the group consisting of gastric cancer, lymphoma, liver cancer, leukemia, renal tumor, lung cancer, small intestinal cancer, bone cancer, prostate cancer, colorectal cancer, breast cancer, colon cancer, prostate cancer and adrenal tumors; and the cancer cell thereof expresses PD-L1.

11. The method of claim 10, wherein the subject is human.

* * * * *